US00PP09698P

United States Patent [19]

Morales-Martinez et al.

[11] Patent Number: Plant 9,698

[45] Date of Patent: Nov. 19, 1996

[54] *ABELIA×GRANDIFLORA* 'SUNRISE'

[75] Inventors: Jo A. Morales-Martinez, Raleigh; Thomas P. McCracken, Zebulon, both of N.C.

[73] Assignee: Taylor's Nursery, Inc., Raleigh, N.C.

[21] Appl. No.: 512,737

[22] Filed: Aug. 8, 1995

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 8,472 11/1993 Gwaltney ..... Plt./54.1

*Primary Examiner*—James R. Feyrer

*Attorney, Agent, or Firm*—Townsend & Townsend & Crew

[57] ABSTRACT

A new and distinct variety of *Abelia×grandiflora* characterized by its low mounding growth habit, unique yellow variegated foliage in winter; its dark red stems and few flowers. The new variety is further characterized by its drought tolerance, insect and disease resistance and dense branching.

3 Drawing Sheets

DESCRIPTION

This invention relates to a new and distinct variety of *Abelia×grandiflora* plant (*Caprifoliaceae Abelia×grandiflora,* Rehd. of the order Rubiaceae. and designated 'Sunrise'.

*Abelia×grandiflora* was derived from the cross *A. chinensis×A. uniflora.* and the new variety of this application originated as a branch sport from *Abelia×grandiflora* which was discovered in a field of cultivated *Abelia×grandiflora* plants growing at the container nursery of Taylor's Nursery, Inc. located at 3705 New Bern Avenue, Raleigh, N.C. 27610.

Asexual reproduction by cuttings of 'Sunrise' was done under the direction of Thomas P. McCracken at Taylor's Nursery, Inc. Raleigh, N.C. in 1992. Large numbers of plants were reproduced and evaluated for stability. These were found to be completely stable over a number of generations.

'Sunrise' has a number of distinguishing characteristics which make it commercially valuable.

1. It is a compact shrub with low mounding habit and shortened primary branches in a flush. Parent plants are ungainly with an open habit and elongated primary branches that require frequent pruning to make the plants more uniform. The compact growth forms of 'Sunrise' is ideal for mass plantings, low hedges and edging, and does not require frequent pruning to keep the plant looking good.

2. The new stem/branch growth is reddish (Group 46A) apically becoming reddish-purple (Group 59A), a unique trait for *Abelia×grandiflora.* The striking contrast between the branches and the foliage on 'Sunrise' provides a pleasing ornamental characteristic.

3. The foliage is variegated with a yellow marginal band that irregularly extends towards the midrib, and is maintained in both sunny and shaded environments.

4. 'Sunrise' exhibits a reduction in flowers as compared to the parent plants. Flowers are borne sporadically on the plant and in low quantities. Many consumers are allergic to bee stings and the parent plants attract bees in large quantities. The reduction in flower production makes this a desirable trait for many consumers who would have less exposure to bee stings.

In addition to the foregoing, 'Sunrise' exhibits the desirable traits of the parents, such as drought tolerance, good response to fertilization, and no noticeable susceptibility to insects or diseases.

'Sunrise' is distinctive from several cultivars commercially available that might appear superficially similar. These include the only two other variegated selections, 'Conti' and 'Francis Mason'. The chart below contrasts characteristics that can be used to distinguish between these three selections.

| Characteristic | 'Sunrise' | 'Conti' | 'Francis Mason' |
|---|---|---|---|
| Habit | | | |
| Form | Dwarf shrub | Groundcover | Large shrub |
| Height (4 yr) | 62–92 cm | 45–60 cm | 154–185 cm |
| Width (4 yr) | 92–107 cm | 120–150 cm | 123–154 cm |
| Leaves | | | |
| Variegation | Yellow | Cream-White | Yellow |
| Duration | Continuous | Continuous | 2–3 weeks* |
| Winter Color | Orange/Red | Pink/Rose | None |

*In shade the variegation fades completely to green and in sun the variegation fades completely to yellow.

'Sunrise' and 'Conti' have been evaluated side-by-side for the past two years and have demonstrated that the growth habit of 'Sunrise' is low mounding compared to 'Conti' which is a ground cover. Height is clearly and markedly distinct between 'Sunrise' and 'Conti'. In addition, coloration of the variegation is clearly and markedly distinct between 'Sunrise' and 'Conti'. 'Sunrise' maintains its yellow variegation even under heavy shade conditions, whereas 'Conti' loses much of its white variegation under the same conditions.

'Sunrise' is clearly and markedly distinct from 'Francis Mason' also. The distinction is due to the growth habit and retention of foliar variegation. 'Sunrise' maintains its variegation throughout the year, whereas 'Francis Mason' turns completely green in shade and completely yellow in sun.

Concerning other *Abelia×grandiflora* cultivars, 'Sunrise' is readily distinguishable due to its distinct foliar variegation and, as stated, is readily distinguishable from 'Conti' in both growth habit and foliar variegation.

Based upon the side-by-side comparison between 'Sunrise' and 'Conti', 'Sunrise' is clearly not precocious, whereas 'Conti' blooms heavily even as a very young plant.

Figure 1:
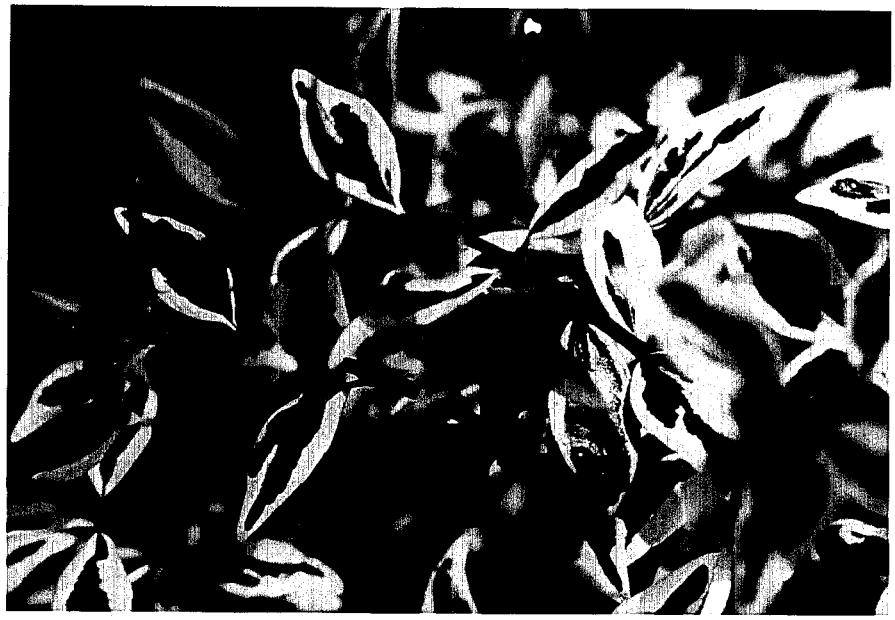
FIG. 1 shows the unusual yellow variegated foliage and dark red stem coloration typical of the new variety during early season growth.
Figure 2:
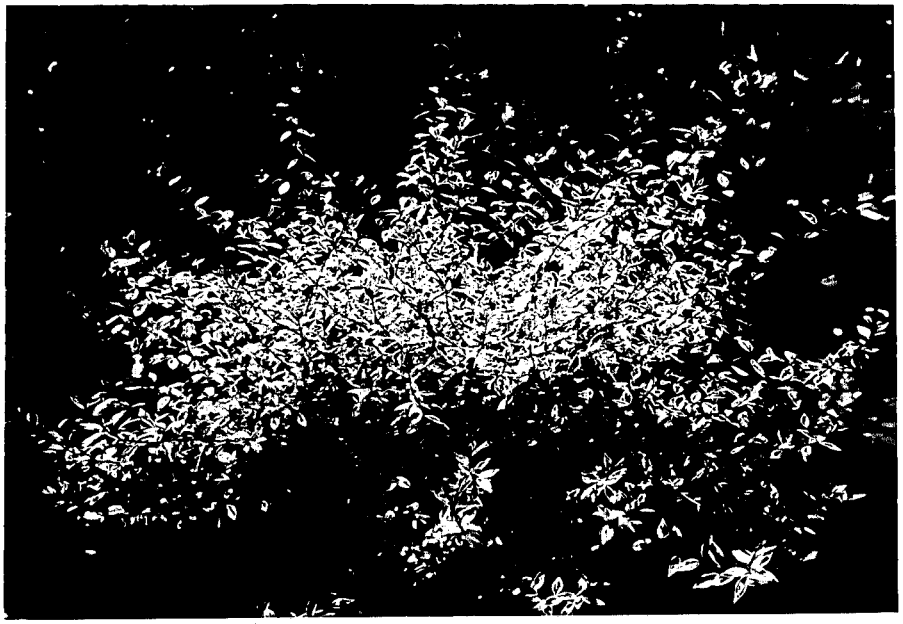
FIG. 2 depicts the low mounding nature of the new variety.
Figure 3:
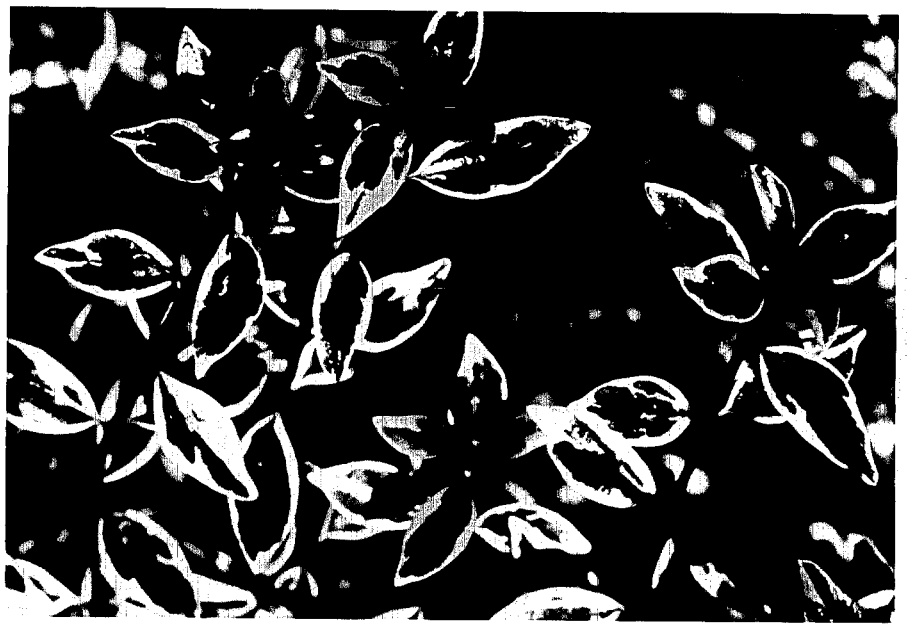
FIG. 3 illustrates the color of mature and immature leaves in full sun exposure.
Figure 4:
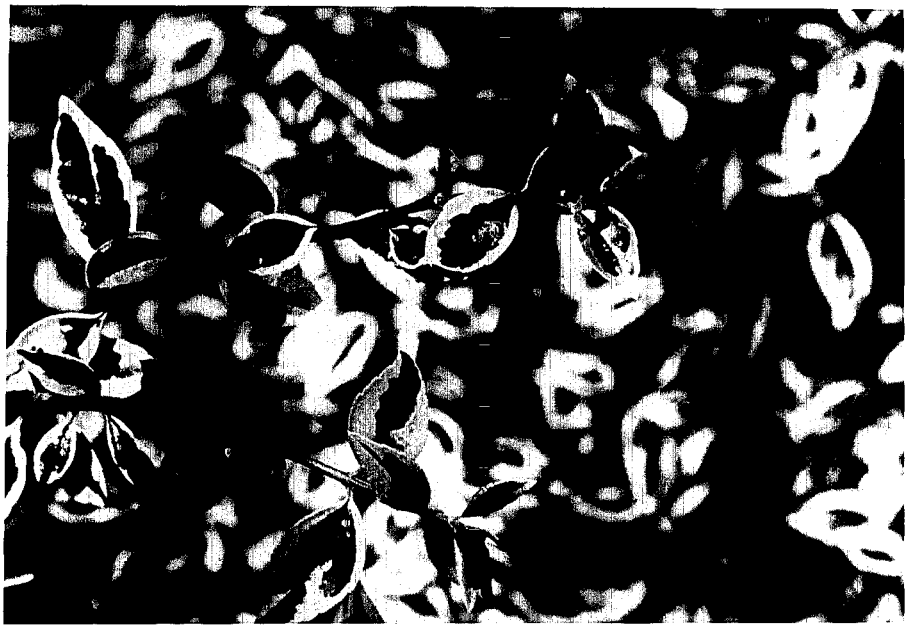
FIG. 4 shows the color of mature and immature leaves in very low light exposure (approximately 85% shade)
Figure 5:
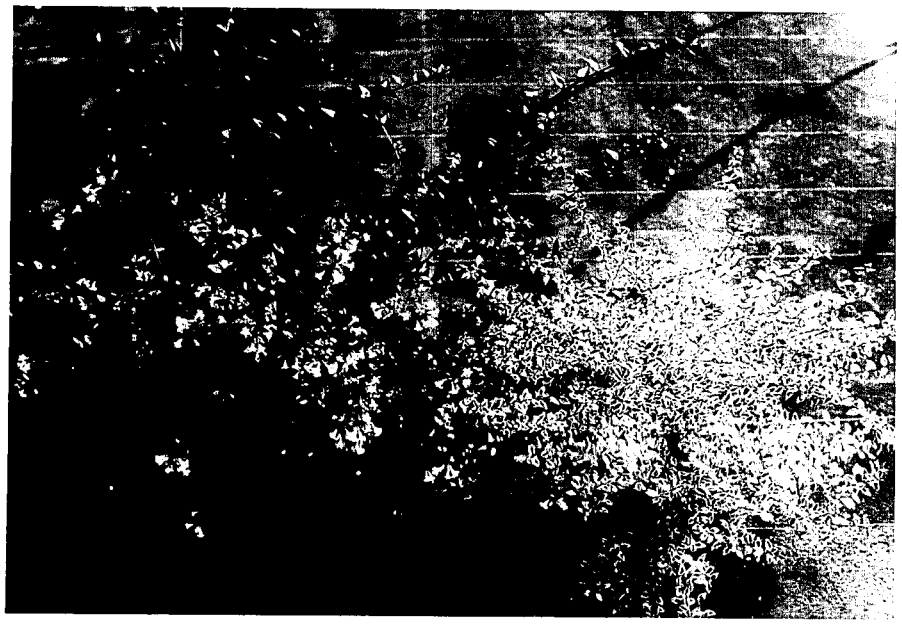
FIG. 5 is a side by side comparison of the species *Abelia×grandiflora* and 'Sunrise' showing the low mounding growth habit and dense branching of 'Sunrise'.

The following is a detailed description of the characteristics of the new variety shown in comparison with the *Abelia×grandiflora* which is its parent and is based upon a three year observation of plants grown in Raleigh, N.C. by methods commonly practiced by commercial nurseries:

| | 'Sunrise' *Abelia × grandiflora* | |
|---|---|---|
| Height | 122 cm | 183 cm |
| Width | 152 cm | 183 cm |
| Leaf-width | 1 cm | 1.8 cm |
| Leaf-length | 2.3 cm | 3.8 cm |
| Stem | dark red | pink |
| Flower | white-rarely blooms | white |
| Foliage | green-yellow variegated | green |

SPECIFIC DESCRIPTION

The colors described in the following description are according to the nearest colors of the color chart of The Royal Horticultural Society.

Plant form:

*Habit.*—Evergreen or semi-evergreen, compact, dwarf shrub with cane-like growth, currently (four years growth), 62–92 cm tall, and 120–150 cm wide. Based upon comparison with typical parent plants, expected height is 92–154 cm and expected spread is 154–185 cm in ten years.

*Branches.*—Primary branches numerous, erect, spreading, reaching a length of 27.5–33 cm in a single flush, with 3–4 flushes per year. Secondary branches: Lateral, short (=pins), commonly 10–15 cm long. 'Sunrise' branches are shorter than those of the parent plants which exhibit primary branches 77–103 cm in a flush.

*Leaves.*—Arrangement opposite. Leaves in whorls of threes that occasionally appear in strong vigorous primary shoots of the parent have not been observed. Leaves are simple in type. Their duration is evergreen or semi-evergreen in colder climates and are ecliptic-ovate in shape. They are generally small in size 2–2.5 cm long, 0.8–1.3 cm wide. Margins are crenate to weakly serrately crenate, teeth occurring primarily above the widest portion of the leaf. The adaxial surface is lustrous, glabrous, medium to dark green with yellow variegation along the margins and occasionally variegation irregularly extending toward midrib along major veins; primary lateral veins obscure. Abaxial surface is glabrous, light green, variegation following pattern on adaxial surface; primary lateral veins 3–5, conspicuous, secondary veins reticulate. Apex is acute to broadly acute. Petiole is 2–3 mm.

*Flowers.*—Type and location: Inflorescences, dichasia to compound dischasia, axillary or terminal on pins, few-flowered, 3–7 flowered, borne on new growth. Flowers are infrequently produced, sporadic on plant.

*Pedicels.*—Shape is 3–6 mm. Calyx is salverform, connate below with 2–5 free lobes. Corolla is campanulate-funnel form, weakly zygomorphic, white, circa 2 cm long, lobes 5. A pinkish flush or hew observed in some cultivars has not been observed in 'Sunrise'. Stamens: Four, didynamous, inserted at base of corolla tube. Pistil is solitary; ovary inferior.

*Fruit.*—Type: Fruits not produced. Type of parents is a 1-seeded leathery cypsela surrounded and crowned by the persistent calyx.

Colors:

New growth of the primary stems and pins in a flush is reddish (Red Group 46A) apically becoming reddish–purple (Red-Purple Group 59A) with age in the first year; succeeding seasons becoming woody.

Leaves are variegated and contain three primary colors: a yellow color (Greyed-Yellow Group 160A), which consists of a margin around the leaf edge. A green center (Green Group 136A-B) and a combination of these colors (Yellow-Green Group 145C) which is also found in the central portion of the leaves. The green (Green Group 126A-B) center of the leaf covers approximately 60–85% of the leaf. The Yellow-Green Group (145C) is probably derived from a periclinal chimera. 'Sunrise' is distinctly colored differently dependant upon the light exposure. Plants grown in strong, direct light consist of the colors Greyed-Yellow Group 160A, Yellow-Green Group 145C, and Green Group 136A-B. The immature leaves are primarily Greyed-Orange Group 169A-B and Greyed-Orange Group 168B. Under extremely low light conditions, (approximately 85% shade) the plants consist of the colors Greyed-Yellow Group 160A, Green Group 138A-C, and Green Group 137A. The immature leaves are primarily Greyed-Yellow Group 160A-B and Green Group 136A. The winter leaf color is also independent of light exposure and consists of the colors of Greyed-Orange Group 170A-B, Greyed-Orange Group 169A, Yellow-Orange Group 15B-C, and Green Group 136A-B. The variation of leaf coloring results in the differing chlorophyll content of the leaves.

Culture:

Performs well under a wide range of conditions. Tolerates full sun to nearly full shade (85% shade) exposure while still maintaining its variegation. Prefers reasonably moist soil conditions but is also fairly drought tolerate. Responds well to fertilization.

Insects and diseases: No noticeable susceptibility to invasion by insects or to diseases.

I claim:

1. We claim the new and distinct variety of *Abelia× grandiflora* herein described and illustrated and identified by the characteristics enumerated above.

* * * * *